United States Patent
Saudan et al.

(10) Patent No.: US 8,198,488 B2
(45) Date of Patent: Jun. 12, 2012

(54) HYDROGENATION OF ESTERS WITH RU/BIDENTATE LIGANDS COMPLEXES

(75) Inventors: Lionel Saudan, Geneva (CH);
Christophe Saudan, Geneva (CH);
Michel Alfred Joseph Saudan, legal representative, Geneva (CH); Sylvia Joyeuse Adélaide Ada Saudan, legal representative, Geneva (CH)

(73) Assignee: Firmenich SA, Geneva (CH)

( * ) Notice: Subject to any disclaimer, the term of this patent is extended or adjusted under 35 U.S.C. 154(b) by 380 days.

(21) Appl. No.: 12/515,934

(22) PCT Filed: Nov. 22, 2007

(86) PCT No.: PCT/IB2007/054746
§ 371 (c)(1),
(2), (4) Date: Dec. 17, 2009

(87) PCT Pub. No.: WO2008/065588
PCT Pub. Date: Jun. 5, 2008

(65) Prior Publication Data
US 2010/0286452 A1    Nov. 11, 2010

(30) Foreign Application Priority Data
Nov. 27, 2006 (WO) .................. PCT/IB2006/054449

(51) Int. Cl.
*C07C 27/04* (2006.01)
(52) U.S. Cl. ......... 568/885; 568/814; 502/162; 502/167
(58) Field of Classification Search .................. None
See application file for complete search history.

(56) References Cited

U.S. PATENT DOCUMENTS

| | | | |
|---|---|---|---|
| 6,720,439 B1 * | 4/2004 | Ohkuma et al. | 556/8 |
| 7,378,560 B2 * | 5/2008 | Ohkuma et al. | 568/881 |
| 7,763,758 B2 * | 7/2010 | Saudan et al. | 568/814 |
| 7,989,665 B2 * | 8/2011 | Saudan et al. | 568/592 |
| 8,124,816 B2 * | 2/2012 | Saudan et al. | 568/885 |
| 2002/0095056 A1 | 7/2002 | Cobley et al. | 564/423 |

FOREIGN PATENT DOCUMENTS
WO  WO 2006/046508 A1  5/2006
WO  WO 2006/106483 A1  10/2006

OTHER PUBLICATIONS

International Search Report PCT/IB2007/054746, Dated May 13, 2008.
Teunissen, Herman T. et al., "Homogeneous Ruthenium Catalyzed Hydrogenation of Esters to Alcohols", Institute of Molecular Chemistry, Chem. Commun., pp. 1367-1368, (1998).
Doucet, Henri et al., "*trans*-[RuCl$_2$(phosphane)$_2$(1,2-diamine)] and Chiral *trans*-[RuCl$_2$(diphosphane)(1,2-diamine):Shelf-Stable Precatalysts for the Rapid, Productive, and Stereoselective Hydrogenation of Ketones", Agnew Chem. Int., vol. 37, No. 12, pp. 1703-1707, (1998).
Ohkuma, Takeshi et al., "Asymmetric Hyrogenation of Ketones with Polymer-Bound BINAP/Diamine Ruthenium Catalysts", Adv. Synth. Catal., vol. 343, No. 4, pp. 369-375, (2001).

* cited by examiner

*Primary Examiner* — Sudhakar Katakam
(74) *Attorney, Agent, or Firm* — Winston & Strawn LLP

(57) ABSTRACT

The present invention relates to processes for the reduction by hydrogenation, using molecular H2, of a substrate containing one or two esters, or lactones, functional groups into the corresponding alcohol, or diol, with the process being carried out in the presence of a base and at least one catalyst or pre-catalyst in the form of a ruthenium complex, wherein the ruthenium is coordinated by a diphosphine bidentate ligand (PP ligand) and a diamino bidentate ligand (NN ligand) that includes at least one substituted α-carbon and one primary amine as one of the coordinating atoms.

12 Claims, No Drawings

HYDROGENATION OF ESTERS WITH RU/BIDENTATE LIGANDS COMPLEXES

This application is a 371 filing of International Patent Application PCT/IB2007/054746 filed Nov. 22, 2007.

TECHNICAL FIELD

The present invention relates to the field of catalytic hydrogenation and, more particularly, to the use of specific chiral Ru complexes with bidentate PP and NN ligands, in hydrogenation processes for the reduction of esters or lactones into the corresponding alcohol or diol respectively.

PRIOR ART

Reduction of an ester functional group to the corresponding alcohol is one of the fundamental reactions in organic chemistry, and is used in a large number of chemical processes. In general, two main types of processes are known to achieve such a transformation. Such types of processes are the following:
a) hydride processes, in which a silyl or metal hydride salt, such as $LiAlH_4$, is used;
b) hydrogenation processes, in which molecular hydrogen is used.

From a practical point of view, hydrogenation processes are more attractive as they can be run using small amounts of catalyst (typically 10 to 1000 ppm relative to the substrate) and in the presence of small quantities or even in the absence of solvent. Furthermore, hydrogenation processes do not require the use of highly reactive and expensive hydrides, and do not produce important amounts of aqueous waste.

One of the mandatory and characterizing elements of hydrogenation processes is the catalyst or the catalytic system which is used to activate the molecular hydrogen in view of the reduction. The development of useful catalysts or catalytic systems for the hydrogenation of an ester functional group represents still an important, difficult and unpredictable task in chemistry.

Amongst the few catalysts or catalytic systems known to perform such reductions one may cite the ruthenium/phosphine complexes, obtained by the reaction of ruthenium oxide or carboxylate precursor with a mono-, di- or tri-phosphine ligand (an example of which is described by Elsevier et al. in Chem. Commun., 1998, 1367). In this type of complex the ruthenium metal is coordinated only by "acac" ligands and phosphine atoms, limiting thus the diversity of the ligand structure and coordination sphere around the metal center. As a consequence of such little diversity, the tuning of the activity and of the performance of the hydrogenation process is not easy. Furthermore, the experimental conditions require very high pressures (at least 70-130 bars) and temperatures (120-180° C.).

However, there is still a need for hydrogenation processes using alternative catalysts or pre-catalysts, thus to have a greater diversity in the ligand structures and coordination spheres around the metal center and allowing a higher, and possibly easier, diversity in the experimental conditions and in the type of reaction which can be performed.

DESCRIPTION OF THE INVENTION

In order to overcome the problems aforementioned, the present invention relates to processes for the reduction by hydrogenation, using molecular $H_2$, of a $C_3$-$C_{70}$ substrate containing one, two or three esters, or lactones, functional groups into the corresponding alcohol, or diol, characterized in that said process is carried out in the presence of a base and at least one catalyst or pre-catalyst in the form of a ruthenium complex wherein the ruthenium is coordinated by a diphosphine bidentate ligand (PP ligand) and a diamino bidentate ligand (NN ligand) comprising at least one substituted α-carbon (relative to a coordinating nitrogen atom).

According to a particular embodiment of the invention, the substrate can be a compound of formula (I)

wherein $R^a$ and $R^b$ represent, simultaneously or independently, a linear, branched or cyclic $C_1$-$C_{30}$ aromatic, alkyl or alkenyl group, optionally substituted; or $R^a$ and $R^b$ are bonded together and form a $C_3$-$C_{20}$, preferably $C_4$-$C_{20}$, saturated or unsaturated group, optionally substituted.

The corresponding alcohols (i.e. (II-a) and (II-b)), or the corresponding diol (II'), of said substrate (I), are of formula

wherein $R^a$ and $R^b$ are defined as in formula (I).

A compound of formula (II) (i.e. II-a or II-b) will be obtained in the case where $R^a$ and $R^b$ are not bonded together, while a compound of formula (II') will be obtained in the case where $R^a$ and $R^b$ are bonded together.

It is understood that by "a linear, branched or cyclic . . . aromatic, alkyl, or alkenyl group" it is meant that said $R^a$ or $R^b$ can be in the form of, e.g., a linear alkyl group or can also be in the form of a mixture of said type of groups, e.g. a specific $R^a$ may comprise a linear alkyl, a branched alkenyl, a (poly) cyclic alkyl and an aryl moiety, unless a specific limitation to only one type is mentioned. Similarly, in all the below embodiments of the invention when a group is mentioned as being in the form of more than one type of topology (e.g. linear, cyclic or branched) and/or unsaturation (e.g. alkyl, aromatic or alkenyle) it is meant also a group which may comprise moieties having any one of said topologies or unsaturations, as above explained.

A particular embodiment of the invention's process is shown in Scheme 1:

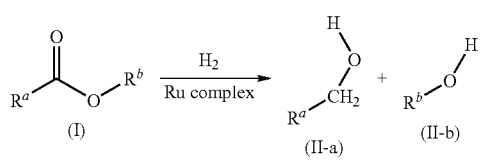

According to a further embodiment of the invention, the substrate is an ester, or lactone, that will provide an alcohol, or a diol, that is useful in the pharmaceutical, agrochemical or perfumery industry as final product or as an intermediate. Particularly preferred substrate is an ester, or lactone, that will provide an alcohol, or diol, which is useful in the perfumery industry as final product or as an intermediate.

According to another embodiment of the invention, the substrate is a $C_5$-$C_{30}$ compound of formula (I), and in particular one may cite those wherein $R^a$ and $R^b$ represent simultaneously or independently a linear, branched or cyclic $C_1$-$C_{30}$ aromatic or alkyl group optionally substituted, or a cyclic $C_5$-$C_{30}$ alkenyl group optionally substituted; or $R^a$ and $R^b$ are bonded together and form a $C_4$-$C_{20}$ saturated or unsaturated linear, branched, mono-, di- or tri-cyclic group, optionally substituted.

According to a further embodiment of the invention, the substrate is a $C_5$-$C_{20}$ compound of formula (I), wherein $R^a$ and $R^b$ represent simultaneously or independently a linear, branched or cyclic $C_5$-$C_{18}$ aromatic or alkyl group, optionally substituted, or a cyclic $C_5$-$C_{18}$ alkenyl group, optionally substituted; or $R^a$ and $R^b$ are bonded together and form a $C_4$-$C_{20}$ saturated or unsaturated linear, branched, mono-, di- or tri-cyclic group, optionally substituted.

Possible substituents of $R^a$ and $R^b$ are one, two or three halogen, $OR^c$, $NR^c_2$ or $R^c$ groups, in which $R^c$ is a hydrogen atom, a halogenated $C_1$-$C_2$ group or a $C_1$ to $C_{10}$ cyclic, linear or branched alkyl, or alkenyl group, preferably a $C_1$ to $C_4$ linear or branched alkyl or alkenyl group. As other possible substituents one may also cite a group $COOR^c$, which can also be reduced to the corresponding alcohol during the invention's process, according to the molar amount of $H_2$ used, as well known by a person skilled in the art.

Non-limiting examples of substrates are alkyl cinnamates, sorbates or salycilates, alkyl esters of natural (fatty or not) acids, Sclareolide, spirolactones, allylic ester, di alkyl diesters, (un)substituted benzoic esters, and β-γ unsaturated esters. In particular, the substrate can be selected from the group consisting of sclareolide, $C_9$-$C_{15}$ spirolactones and $C_1$-$C_4$ alkyl esters of 4-methyl-6-(2,6,6-trimethyl-1-cyclohexen-1-yl)-3-hexenoic acid. One can also cite the di alkyl esters of 1,4-dicarboxylate-cyclohexane, the di $C_{1-5}$ alkyl esters of the $C_{2-10}$ alkanediyl-dicarboxylates, $C_{1-5}$ alkyl cyclopropanecarboxylates, mono-, di- or tri-methoxybenzoic esters.

According to a particular embodiment of the invention, the substrate (I) is a racemic or optically active compound. Indeed in such a case, due to the fact that the invention complex may comprises at least one ligand which is in a optically active form, it is possible to selectively or preferentially hydrogenate one particular enantiomer of such substrate (kinetic resolution of the substrate).

The process of the invention is characterized by the use, as catalyst or pre-catalyst (hereinafter referred to as complexes unless specified otherwise), of a ruthenium complex as described above. The complex can be in the form of an ionic or neutral species.

According to an embodiment of the invention, the ruthenium complex can be of the general formula $$[Ru(PP)(NN)(S)_{2-n}Y_n](Y)_{2-n} \quad (1)$$

wherein n represents 0, 1 or 2;
S represents a neutral $C_1$-$C_{26}$ neutral monodentate ligand;
PP represents a $C_6$-$C_{60}$ bidentate ligand wherein the coordinating groups are two phosphino groups;
NN represents a $C_3$-$C_{40}$ bidentate ligand wherein the coordinating groups are two amino groups, at least one of said amino groups is a primary amine (i.e. a $NH_2$), and said ligand comprising at least one substituted α-carbon; and
each Y represents, simultaneously or independently, a hydrogen or halogen atom, a $BH_4$ or $AlH_4$ group, a hydroxyl group, or a $C_1$-$C_6$ alkoxy or carboxylic radical.

By the expression "said ligand comprising at least one substituted α-carbon", mentioned for the ligand NN, it is meant a ligand wherein at least one of the carbon atoms to which one of said amino groups is bound (the α-carbon) is not a $CH_3$— or —$CH_2$— group. Preferentially, said α-carbon is the one to which the coordinating $NH_2$ group is bound.

The catalyst or pre-catalyst can be also in a supported form, e.g. bounded to a polymer.

The monodentate ligand can be a phosphine, like $PPh_3$, CO or even a solvent. By the term "solvent" it has to be understood the usual meaning in the art and in particular compounds used as diluent in the preparation of the complex or during the invention's process. Non limiting examples of such solvent are dimethylsulfoxide, acetonitrile, dimethylformamide, an alcohol (e.g. an $C_1$-$C_4$ alcohol), or also THF, acetone, pyridine or a $C_3$-$C_8$ ester or the substrate of the invention's process.

In a particular embodiment of the invention, said NN or PP ligand may be a $C_3$-$C_{40}$ compound.

In a particular embodiment of the invention, in formula (1), each Y represents, simultaneously or independently, a hydrogen or chlorine atom, a hydroxy radical, a $C_1$ to $C_6$ alkoxy radical, such as a methoxy, ethoxy or isopropoxy radical, or a $C_1$ to $C_6$ acyloxy radical such as a $CF_3COO$ or $CH_3COO$ or $CH_3CH_2COO$ radical. More preferably, each Y represents, simultaneously or independently, a hydrogen or chlorine atom, a methoxy, ethoxy or isopropoxy radical, or a $CH_3COO$ or $CH_3CH_2COO$ radical.

According to a particular embodiment of the invention, there can be used as complex a compound of formula $$[Ru(PP)(NN)Y_2] \quad (2)$$

wherein PP, NN and Y have the meaning indicated above.

According to any one of the above-mentioned embodiments, the bidentate PP ligand is an optically active compound of formula

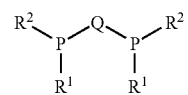

wherein
$R^1$ and $R^2$, when taken separately, represent, simultaneously or independently, a linear, branched or cyclic $C_1$ to $C_8$ alkyl or alkenyl group optionally substituted, a $C_6$ to $C_{10}$ aromatic group optionally substituted, or an $OR^3$ or $NR^3R^4$ group, $R^3$ and $R^4$ being a $C_1$ to $C_8$ alkyl or alkenyl group; the groups $R^1$ and $R^2$, bonded to the same P atom, when taken together, may form a saturated or unsaturated ring optionally substituted, having 5 to 10 atoms and including the phosphorus atom to which said $R^2$ and $R^1$ groups are bonded; and Q represents:

a group of formula

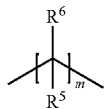

(i)

wherein m is an integer from 1 to 5, and $R^5$ and $R^6$ represent, simultaneously or independently, a hydrogen atom, a linear, branched or cyclic $C_1$ to $C_{10}$ alkyl or alkenyl group optionally substituted, a $C_6$-$C_{10}$ aromatic group optionally substituted, or an $OR^7$ or $NR^7R^8$ group, $R^7$ and $R^8$ being a linear, branched or cyclic $C_1$ to $C_{10}$ alkyl or alkenyl group; two distinct $R^6$ and/or $R^5$ groups, taken together, may form a $C_5$ to $C_8$, or even up to $C_{10}$, saturated ring optionally substituted, including the carbon atoms to which each of said $R^6$ or $R^5$ group is bonded; or a group of formula

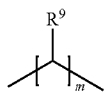

(ii)

wherein m is an integer from 2 to 4, and two distinct adjacent $R^9$ groups, taken together, form a $C_5$ to $C_8$, or even up to $C_{10}$, aromatic ring optionally substituted or a $C_5$-$C_{12}$ metallocenediyl optionally substituted, including the carbon atoms to which each of said $R^9$ group are bonded; or three distinct adjacent $R^9$ groups, taken together, form a naphthalene ring optionally substituted, including the carbon atoms to which each of said $R^9$ groups are bonded.

According to an embodiment, by "aromatic group or ring" it is meant a phenyl or naphthyl derivative.

According to another embodiment of the invention, Q represents a linear $C_2$-$C_5$ alkanediyl radical optionally substituted, a ferrocenediyl optionally substituted or a biphenyldiyl or binaphthildiyl radical optionally substituted.

Possible substituents of $R^1$ to $R^9$ and Q are one or two halogen, $C_1$ to $C_{10}$ alkoxy or polyalkyleneglycols groups, halo- or perhalo-hydrocarbon, $COOR^d$, $NR^d_2$, quaternary amine or $R^d$ groups, wherein $R^d$ is a $C_1$ to $C_6$ alkyl, or a $C_5$ to $C_{12}$ cycloalkyl, aralkyl (such as benzyl, phenethyl, etc) or aromatic group, the latter being also optionally substituted by one, two or three halogen, sulfonates groups or $C_1$-$C_8$ alkyl, alkoxy, amino, nitro, sulfonates, halo- or perhalo-hydrocarbon or ester groups. By "halo- or perhalo-hydrocarbon" it is meant groups such as $CF_3$ or $CClH_2$ for instance.

In a particular embodiment of formula (3), PP is a bidentate ligand wherein $R^1$ and $R^2$ represent, simultaneously or independently, a linear, branched or cyclic $C_1$ to $C_6$ alkyl group optionally substituted, a phenyl or naphthyl group optionally substituted; the groups $R^1$ and $R^2$, bonded to the same P atom, taken together, form a saturated or unsaturated ring optionally substituted, having 5, 6 or 7 atoms and including the phosphorus atom to which said $R^1$ and $R^2$ groups are bonded; and Q represents:

a group of formula

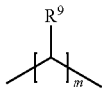

(iv)

wherein m is an integer from 1 to 3, and two distinct adjacent $R^9$ groups, taken together, form a $C_5$ to $C_{10}$ aromatic ring optionally substituted or a $C_5$-$C_{12}$ ferrocenediyl optionally substituted, including the carbon atoms to which each of said $R^9$ group are bonded; or three distinct adjacent $R^9$ groups, taken together, form a naphthalene ring optionally substituted, including the carbon atoms to which each of said $R^9$ group are bonded.

Possible substituents of $R^1$ to $R^9$ and Q, in particular when said groups are or contain phenyl groups or moieties, are one or two halogen, $CF_3$ groups or $C_1$ to $C_5$ alkoxy or polyalkyleneglycols groups, $COOR^d$, $NR^d_2$ or $R^d$ groups, wherein $R^d$ is a $C_1$ to $C_4$ alkyl, or a $C_{5-6}$ cycloalkyl, aralkyl or aromatic group, the latter being also optionally substituted as above defined.

Furthermore, in all the above embodiments, a particularly appreciated mode of realization is the one where said $R^1$ and $R^2$ groups are aromatic groups optionally substituted.

Compound (1) can be in a supported form. As typical support one may cite Takeshi Ohkuma et al, in Advanced Synth. Catal. 2001, 343, 369. For instance in the PP ligand of the above-mentioned embodiments, the Q group may comprise a substituent $OR^{15}$ as defined hereinbelow.

A particular embodiment of formula (3) is represented by formula

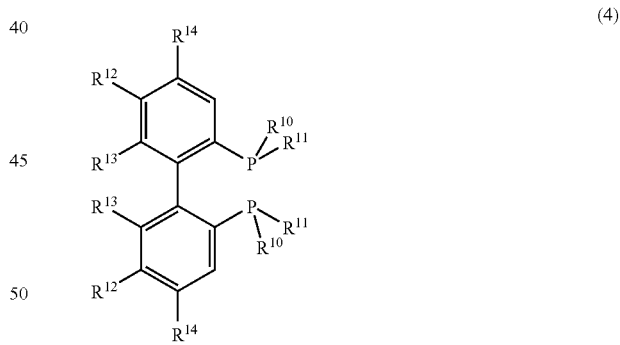

(4)

wherein $R^{10}$ and $R^{11}$ when taken separately, represent, simultaneously or independently, a linear, branched or cyclic $C_1$ to $C_5$ alkyl group optionally substituted, a $C_6$ to $C_{10}$ aromatic group optionally substituted; the groups $R^{10}$ and $R^{11}$, bonded to the same P atom, when taken together, may form a saturated or unsaturated ring optionally substituted, having 5 to 10 atoms and including the phosphorus atom to which said $R^{10}$ and $R^{11}$ groups are bonded;

$R^{12}$, $R^{13}$ and $R^{14}$ when taken separately, represent, simultaneously or independently, a linear, branched or cyclic $C_1$ to $C_5$ alkyl or alkoxy group optionally substituted, a phenyl group optionally substituted; one of said $R^{12}$, $R^{13}$ and $R^{14}$ being optionally a $OR^{15}$ group, $R^{15}$ representing a unit of the type Z-B'-, B' being a group linking the polymer Z and the ligand, selected from among the groups —(CH$_2$)$_2$—(O—C$_2$H$_4$)$_x$— or —C(O)—(CH$_2$)$_2$—C(O)—NH—(CH$_2$)2-(O—C$_2$H$_4$)$_y$— are preferred, in which x is a whole number of about 60, —C(O)—, —(CH$_2$)$_v$- or —NH—C(O)—(CH$_2$)$_v$—C(O)—, v being a whole number from 1 to 4, and Z being a polymer or copolymer selected from among silica, polystyrene, the polyamides, the grafted copolymers of polystyrene and of polyoxyethylene of the Tentagel® type, the functionalised polystyrene of the Merrifield resin type, aminomethylated polystyrene, or [4-(hydroxymethyl)phenoxymethyl] polystyrene ("Wang resin");
the two R$^{13}$$_5$ or the R$^{12}$ and R$^{13}$ bounded to the same phenyl group, can be taken together to form a ring optionally substituted, having 5, 6 or 7 atoms and including the carbon atoms to which said R$^{13}$ and/or R$^{12}$ groups are bonded; at least one of said ring being optionally substituted by a OR$^{15}$ group as defined above.

Possible substituents of R$^{10}$ to R$^{14}$, in particular when said groups are or contain phenyl groups or moieties, are one or two halogen, CF$_3$ groups or C$_1$ to C$_5$ alkoxy or polyalkyleneglycols groups, COOR$^d$, NR$^d$$_2$ or R$^d$ groups, wherein R$^d$ is a C$_1$ to C$_4$ alkyl, or a C$_{5-6}$ cycloalkyl, aralkyl or aromatic group, the latter being also optionally substituted as above defined.

The Z polymers or copolymers are the state-of-art. The preferred ones are the resin of the "Wang" type, polystyrene or a resin of the so-called "Tentagel" type.

According to a further embodiment of the invention the complexes of formula (4) are of formula (5) (BINAP derivatives)

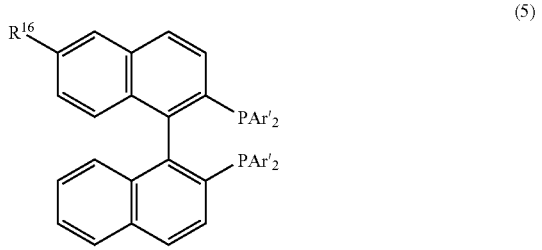

(5)

in which Ar' represents a phenyl group optionally substituted, and R$^{16}$ represents a hydrogen atom or a OR$^{15}$ as defined above. Optional substituents can be the one as defined above for R$^{10}$. Particularly appreciated are the ligands (5) wherein R$^{16}$ represents a hydrogen atom.

According to a particular embodiment of the invention, particularly appreciated ligands PP are the C$_{14}$-C$_{44}$ derivatives of formula (3) and comprising one of the following moieties:
a metallocene-1,1'-diphosphine of formula

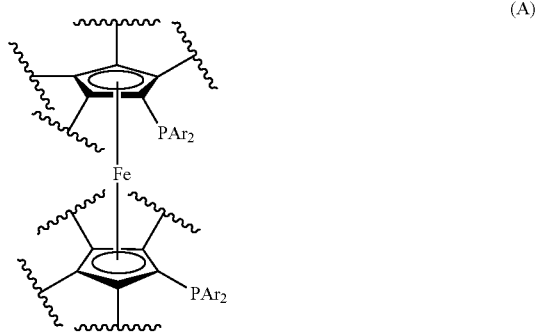

(A)

a α,α'-bis(naphthalene)-β,β'-diphosphine of formula

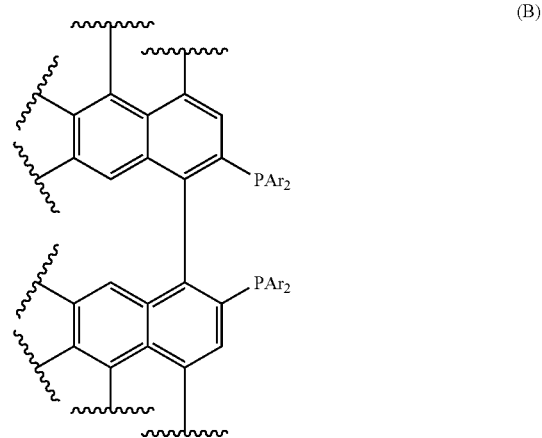

(B)

or a α,α'-bis(benzene)-β,β'-diphosphine of formula

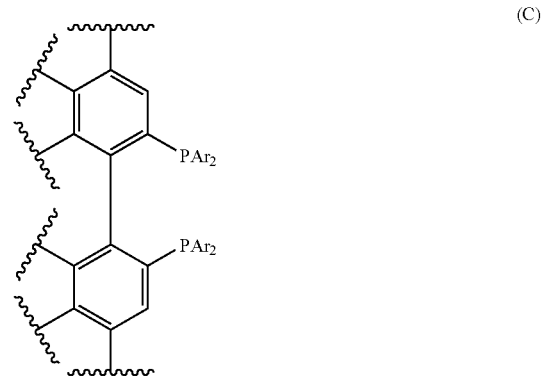

(C)

wherein each Ar represents a C$_6$ to C$_{10}$ aromatic group as defined for R$^{10}$ hereinabove.

According to any one of the above mentioned embodiments, said PP ligand further comprise as coordinating atom at least one triaryl-phosphino group (i.e. PAr$_3$, wherein Ar means an aromatic group), an alkyl-diaryl-phoshino group (i.e. P(alk)Ar$_2$, wherein Ar means an aromatic group and Alk means a non aromatic group) or an dialkyl-aryl-phoshino group (i.e. P(alk)$_2$Ar, wherein Ar means an aromatic group and Alk means a non aromatic group). According to a further development of said embodiment the two coordinating phosphino group of the PP ligand are triaryl-phosphine groups.

According to any one of the above-mentioned embodiments, the NN bidentate ligand is a racemic or an optically active compound comprising at least one substituted α-carbon. Said NN ligand can be of formula

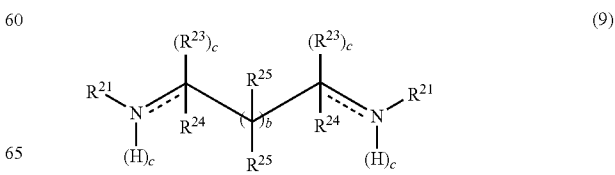

(9)

wherein the dotted line indicates a single or double bond, provided that only one dotted line per nitrogen atom may indicate a double bond;
b represents 0, 1 or 2;
$R^{21}$ represents a hydrogen atom or a $R^{21'}R^{22}CH$ group, or, if the dotted line indicates a single bond may also represent a $R^{21'}R^{22}C=$ group;
c is 0 or 1 when the carbon-nitrogen bond with the dotted line represents a single or double bond respectively; and
$R^{21'}$, $R^{22}$, $R^{23}$, $R^{24}$, and $R^{25}$ represent, simultaneously or independently, a hydrogen atom, a linear, branched or cyclic $C_1$ to $C_{10}$ alkyl or alkenyl group optionally substituted, a $C_6$-$C_{10}$ aromatic group optionally substituted; $R^{21'}$ and $R^{24}$, taken together, may form a saturated or unsaturated heterocycle, optionally substituted and optionally containing one or two additional nitrogen or oxygen atoms, containing 5 to 10 atoms and including the carbon atoms and the N atom to which said $R^{21'}$ or $R^{24}$ are bonded (such as a pyridine ring or a 2-pyrrolidine, a 2-piperidine or a 2-morpholine); $R^{23}$ and $R^{24}$, or $R^{24}$ and $R^{25}$, when taken together, form a saturated or unsaturated ring optionally substituted, having 5 to 12 atoms and including the carbon atom to which said $R^{23}$, $R^{24}$ or $R^{25}$ groups are bonded; with the proviso that at least one of said $R^{23}$ or $R^{24}$ groups are not a hydrogen atom;
provided that at least one $R^{24}$ or $R^{22}$ is not a hydrogen atom, and provided that at least one coordinating amino group is a primary amine (i.e. a $NH_2$ group or at least one $R^{21}$ is a hydrogen atom).

According to an embodiment, by "aromatic group or ring" it is meant a phenyl or naphthyl derivative.

Possible substituents of $R^{21'}$, $R^{21}$ to $R^{25}$ are one or two halogen, $C_1$ to $C_{10}$ alkoxy or polyalkyleneglycols groups, halo- or perhalo-hydrocarbon, $COOR^e$, $NR^e{}_2$, quaternary amine or $R^e$ groups, wherein $R^e$ is a $C_1$ to $C_6$ alkyl, or a $C_5$ to $C_{12}$ cycloalkyl, aralkyl (such as benzyl, phenethyl etc.) or aromatic group, the latter being also optionally substituted by one, two or three halogen, sulfonates groups or $C_1$-$C_8$ alkyl, alkoxy, amino, nitro, sulfonates, halo- or perhalo-hydrocarbon or ester groups. By "halo- or perhalo-hydrocarbon" it is meant groups such as $CF_3$ or $CClH_2$ for instance.

According to any one of the above-mentioned embodiments, $R^{21'}$, $R^{22}$, $R^{23}$, $R^{24}$, and $R^{25}$ represent, simultaneously or independently, a hydrogen atom, a linear, branched or cyclic $C_1$ to $C_5$ alkyl or alkenyl group optionally substituted, a phenyl group optionally substituted; $R^{21'}$ and $R^{24}$, taken together, may form a saturated or unsaturated heterocycle, optionally substituted and optionally containing one or two additional nitrogen or oxygen atoms, containing 5 or 6 atoms and including the carbon atoms and the N atom to which said $R^{21'}$ or $R^{24}$ are bonded; $R^{23}$ and $R^{24}$, or $R^{24}$ and $R^{25}$, when taken together, form a saturated or unsaturated ring optionally substituted, having 5 or 6 atoms and including the carbon atom to which said $R^{23}$, $R^{24}$ or $R^{25}$ groups are bonded; with the proviso that at least one of said $R^{23}$ or $R^{24}$ groups are not a hydrogen atom.

Alternatively, possible substituents of $R^{21'}$ to $R^{25}$, in particular when said groups are or contain phenyl groups or moieties, are one or two halogen, $CF_3$ groups or $C_1$ to $C_5$ alkoxy or polyalkyleneglycols groups, $COOR^e$, $NR^e{}_2$ or $R^e$ groups, wherein $R^e$ is a $C_1$ to $C_4$ alkyl, or a $C_{5-6}$ cycloalkyl, aralkyl or aromatic group, the latter being also optionally substituted as above defined.

According to a further embodiment of the formula (9), the dotted lines represent a single bond.

According to any one of the above-mentioned embodiments or combination thereof, a particular embodiment of formula (9) is represented by formula

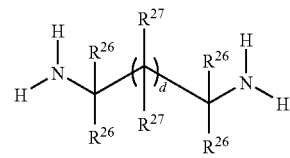

(12)

wherein d represents 0 or 1; and
$R^{26}$ or $R^{27}$ represents each a hydrogen atom or a linear, branched or cyclic $C_1$ to $C_6$ alkyl group or a phenyl group optionally substituted; two $R^{26}$, or one $R^{26}$ and one adjacent $R^{27}$, taken together, may form a $C_3$-$C_5$ alkanediyl or alkenediyl;
provided that at least one $R^{26}$ or is not a hydrogen atom.

Possible substituents of $R^{27}$ or $R^{26}$ are one or two halogen, $C_1$ to $C_5$ alkoxy or polyalkyleneglycols groups, $COOR^e$, $NR^e{}_2$ or $R^e$ groups wherein $R^e$ is a $C_1$ to $C_4$ alkyl, or a $C_{5-6}$ cycloalkyl, aralkyl or aromatic group, the latter being also optionally substituted as defined above.

According to any one of the above-mentioned embodiments or combination thereof, a particular embodiment of formula (12), the NN ligand can be one of the formulae

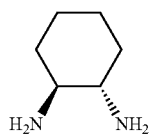

(12')

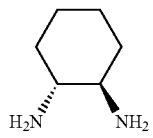

(12")

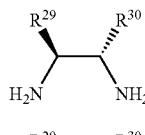

(12''')

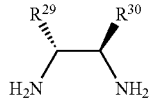

(12'''')

wherein $R^{29}$ represents a $C_1$-$C_6$ alkyl group or a phenyl group optionally substituted, as above defined for $R^{28}$, and $R^3$ represents a hydrogen atom or a $R^{29}$ group.

According to any one of the above-mentioned embodiments, the two coordinating amino group of the NN ligand are primary amino groups (i.e. $NH_2$) or in other words in formula (9) both dotted lines represent a single bond and both $R^{21}$ represent each a hydrogen atom.

Yet, according to a further embodiment, the two coordinating amino groups of the NN ligand are primary amino groups and the two α-carbons are substituted (e.g. in formula (9) the two $R^{24}$ or the two $R^{23}$ are not hydrogen atoms).

According to any one of the embodiments of the invention, at least one of the ligands is in an optically active form. According to a further embodiment the NN ligand is in an optically active form. According to another embodiment, both PP and NN ligands can be in an optically form.

In the present invention, by "optically active form" it is meant here a pure enantiomer or a mixture of enantiomer enriched in a particular enantiomer, in other terms a substrate, complex or ligand in an optically active form is characterised by a e.e. (enantiomeric excess) above 0, typically comprised between 10 and 100% or even between 50 and 100% or between 90 and 99.9%.

The ligands described above can be obtained by applying standard general methods which are well known in the state of the art and by the person skilled in the art. Many of said ligands NN or PP are even commercially available.

In a general way, the complexes of formula (I) can be prepared and isolated prior to their use in the process according to the general methods described in the literature (for example see H. Doucet et al, Angew. Chem. Int. Ed., 1998, 37, 1703.

It is also understood that the complex of formula (I) can also be obtained in situ from complexes which have a similar formula or are cationic or anionic, for example a complex (1) wherein Y has another meaning. Alternatively can be used a complex of formula [Ru(PP)(Anion)$_2$], which in the presence of a NN ligand are converted into a compound of formula (1). It is also possible to use a complex of formula [Ru(NN)(Anion)$_2$] or [Ru(NN)(Anion)(Arene)](Anion), which in the presence of ligand PP are converted into a compound of formula (1).

To carry out the processes of the invention it is required also to use a base. Said base can be the substrate itself, if the latter is basic, a corresponding alcoholate or any base having preferentially a $pK_a$ above 11. According to a particular embodiment of the invention said base may have a $pK_a$ above 14. It is also understood that preferably said base does not reduce itself a substrate of formula (I). As non-limiting examples one may cite the following type of base: alcoholate, hydroxides, alkaline or alkaline-earth carbonates, phosphazenes, amides, basic alox, siliconates (i.e. silicium derivatives having SiO$^-$ or SiRO$^-$ groups), hydrides such as NaBH$_4$, NaH or KH.

One can cite, as non-limiting examples, alkaline or alkaline-earth metal carbonates, such as cesium carbonate, an alkaline or alkaline-earth metal hydroxides, $C_{1-10}$ amidures, $C_{10-26}$ phosphazene or an alcoholate of formula $(R^{31}O)_2M$ or $R^{31}OM'$, wherein M is an alkaline-earth metal, M' is an alkaline metal or an ammonium $NR^{32}{}_4{}^+$, $R^{31}$ stands for hydrogen or a $C_1$ to $C_6$ linear or branched alkyl radical and $R^{32}$ stands for a $C_1$ to $C_{10}$ linear or branched alkyl radical, such as sodium or potassium alcoholates. Of course, other suitable bases can be used.

According to an embodiment of the invention, said base is an alkaline alcoholate of formula $R^{31}OM'$.

As previously mentioned, the processes of the invention consist in the hydrogenation of a substrate using a ruthenium complex and a base. A typical process implies the mixture of the substrate with the ruthenium complex, a base and optionally a solvent, and then treating such a mixture with molecular hydrogen at a chosen pressure and temperature.

The complexes of the invention, an essential parameter of the process, can be added to the reaction medium in a large range of concentrations. As non-limiting examples, one can cite as complex concentration values those ranging from 50 ppm to 50000 ppm, relative to the amount of substrate. Preferably, the complex concentration will be comprised between 100 and 20000 ppm. It goes without saying that the optimum concentration of complex will depend, as the person skilled in the art knows, on the nature of the latter, on the nature of the substrate and on the pressure of H$_2$ used during the process, as well as the desired time of reaction.

Useful quantities of base, added to the reaction mixture, may be comprised in a relatively large range. One can cite, as non-limiting examples, ranges between 5 to 50000 molar equivalents, relative to the complex (e.g. base/com=5 to 50000), preferably 20 to 2000, and even more preferably between 50 and 1000 molar equivalents.

The hydrogenation reaction can be carried out in the presence or absence of a solvent. When a solvent is required or used for practical reasons, then any solvent current in hydrogenation reactions can be used for the purposes of the invention. Non-limiting examples include aromatic solvents such as toluene or xylene, hydrocarbon solvents such as hexane or cyclohexane, ethers such as tetrahydrofuran or MTBE, polar solvents such as primary or secondary alcohols such as isopropanol or ethanol, or mixtures thereof. The choice of the solvent is a function of the nature of the complex and the person skilled in the art is well able to select the solvent most convenient in each case to optimize the hydrogenation reaction.

In the hydrogenation process of the invention, the reaction can be carried out at a H$_2$ pressure comprised between $10^5$ Pa and $80 \times 10^5$ Pa (1 to 80 bars) or even more if desired. Again, a person skilled in the art is well able to adjust the pressure as a function of the catalyst load and of the dilution of the substrate in the solvent. As examples, one can cite typical pressures of 1 to $50 \times 10^5$ Pa (1 to 50 bar).

The temperature at which the hydrogenation can be carried out is comprised between 0° C. and 120° C., more preferably in the range of between 20° C. and 100° C. Of course, a person skilled in the art is also able to select the preferred temperature as a function of the melting and boiling point of the starting and final products as well as the desired time of reaction or conversion.

EXAMPLES

The invention will now be described in further detail by way of the following examples, wherein the temperatures are indicated in degrees centigrade and the abbreviations have the usual meaning in the art.

All the procedures described hereafter have been carried out under an inert atmosphere unless stated otherwise. Hydrogenations were carried out in stainless steel autoclave. H$_2$ gas (99.99990%) was used as received. All substrates and solvents were distilled from appropriate drying agents under Ar. NMR spectra were recorded on a Bruker AM-400 ($^1$H at 400.1 MHz, $^{13}$C at 100.6 MHz, and $^{31}$P at 161.9 MHz) spectrometer and normally measured at 300 K, in CDCl$_3$ unless indicated otherwise. Chemical shifts are listed in ppm.

The following abbreviations used herein below have the following meaning:
BINAP: 2,2'-bis(diphenylphosphino)-1,1'-binaphthyl;
DPEN: 1,2-diphenyl-1,2-ethylenediamine
PCym: para cymene
TFA: trifluoro acetate
dmf: dimethyl formamide
cod: cyclooctadiene

Example 1

Catalytic Hydrogenation of Esters Using In-Situ Formed Complex [RUCl$_2$(R-BINAP)(S,S-DPEN)]

General procedure for the catalytic hydrogenation of methyl benzoate as substrate:
Under argon, a Keim autoclave was charged with a ruthenium R-BINAP complex precursor (0.01 mmol, 0.05 mol %) and S,S-DPEN (0.01 mmol, 0.05 mol %) followed by THF (2 ml) and the solution stirred for 5 minutes Then a solution of methyl benzoate (20 mmol) in THF (2 ml), followed by more THF (2×1 ml), and a solution of tridecane (1 mmol) in THF (2 ml), as internal standard, followed by more THF (2×1 ml), were successively added to the autoclave. Finally, solid NaOMe (1 mmol, 5 mol %) was added and the autoclave was pressurised with hydrogen gas at 50 bars and placed in a thermostatted oil bath set at 100° C. After 1 hour, the autoclave was removed from the oil bath, and cooled in a cold-water bath. Then, an aliquot (0.4 ml) was taken, diluted with MTBE (5 ml), washed with aq. sat. NH$_4$Cl (5 ml), and filtered over a plug of celite and analyzed by GC.

TABLE 1

Hydrogenation of methyl benzoate using [RuCl₂(R-BINAP)(S,S-DPEN)].

| Test | Ru(R-BINAP)X₂ | Ru(S,S-DPEN)X₂ | Com/Base | GC yield |
|---|---|---|---|---|
| 1 | RuCl₂(R-BINAP)(dmf)₂ | — | 500/50000 | 59% |
| 2 | Ru(R-BINAP)(TFA)₂ | — | 500/50000 | 63% |
| 3 | Ru(R-BINAP)(TFA)₂ | — | 500/50000 | 66%[1] |
| 4 | [RuCl(R-BINAP)(pCym)]Cl | — | 500/50000 | 51% |
| 6 | — | RuHCl(S,S-DPEN)(PPh₃)₂ | 500/50000 | 15% |
| 7 | — | [RuCl(S,S-DPEN)(pCym)]Cl | 500/50000 | 2% |

Com/Base: molar ratio in ppm relative to the substrate of complex and base.
GC yield versus internal standard (in %, analysed by GC) of benzyl alcohol after 1 hour. Reaction conditions: H₂ gas (50 bars), 100° C., 1 h, NaOMe as base and THF (2 M).
[1] Catalyst generated in-situ by pre-heating a solution of [Ru(TFA)₂(cod)] and R-BINAP in MTBE/THF (10/1) at 100° C. for 1 h and the solution used as is for the reaction.

Example 2

Catalytic Hydrogenation of Esters Using In-Situ Formed Complex [RuCl₂(R-BINAP)(S,S-DPEN)] at Various Temperatures General procedure for the catalytic hydrogenation of methyl benzoate as substrate:
Under argon, a Keim autoclave was charged with [RuCl₂(R-BINAP)(dmf)₂] (0.01 mmol, 0.05 mol %) and S,S-DPEN (0.01 mmol, 0.05 mol %) followed by THF (2 ml) and the solution stirred for 5 minutes. Then a solution of methyl benzoate (20 mmol) in THF (2 ml), followed by more THF (2×1 ml), and a solution of tridecane (1 mmol) in THF (2 ml), as internal standard, followed by more THF (2×1 ml), were successively added to the autoclave. Finally, solid NaOMe (1 mmol, 5 mol %) was added and the autoclave was pressurised with hydrogen gas at 50 bars and placed in a thermostatted oil bath set at the desired temperature. After the mentioned time, the autoclave was removed from the oil bath, and cooled in a cold-water bath. Then, an aliquot (0.4 ml) was taken, diluted with MTBE (5 ml), washed with aq. sat. NH₄Cl (5 ml), and filtered over a plug of celite and analyzed by GC.

TABLE 2

Hydrogenation of methyl benzoate using [RuCl₂(R-BINAP)(S,S-DPEN)]

| Test | T [° C.] | time [h] | Com/Base | GC yield |
|---|---|---|---|---|
| 1 | 100 | 1 | 500/50000 | 59% |
| 2 | 60 | 2 | 500/50000 | 73% |
| 3 | 60 | 2 | 500/50000 | 68%[1] |
| 4 | 60 | 2 | 500/50000 | 58%[2] |
| 5 | 60 | 8 | 500/50000 | 94% |
| 6 | 40 | 18 | 500/50000 | 94% |

Com/Base: molar ratio in ppm relative to the substrate of complex and base.
GC yield versus internal standard (in %, analysed by GC) of benzyl alcohol. Reaction conditions: H₂ gas (50 bars), NaOMe as base and THF (2 M).
[1] Catalyst generated in-situ by pre-heating a solution of [RuCl(R-BINAP)(pCym)]Cl with S,S-DPEN in THF at 140° C. for 1 h and the solution used as is for the reaction.
[2] Catalyst generated in-situ by pre-heating a solution of [RuCl(S,S-DPEN)(pCym)]Cl with R-BINAP in THF at 140° C. for 1 h and the solution used as is for the reaction.

Example 3

Catalytic Hydrogenation of Esters Using Complex [RuCl₂(PP)(S,S-DPEN)]

General procedure for the catalytic hydrogenation of methyl benzoate as substrate:
Under argon, a Keim autoclave was charged with [RuCl₂(PP)(dmf)₂] (0.01 mmol, 0.05 mol %) and S,S-DPEN (0.01 mmol, 0.05 mol %) followed by THF (2 ml) and the solution stirred for 5 minutes. Then a solution of methyl benzoate (20 mmol) in THF (2 ml), followed by more THF (2×1 ml), and a solution of tridecane (1 mmol) in THF (2 ml), as internal standard, followed by more THF (2×1 ml), were successively added to the autoclave. Finally, solid NaOMe (1 mmol, 5 mol %) was added and the autoclave was pressurised with hydrogen gas at 50 bars and placed in a thermostatted oil bath set at 60° C. After 2 h, the autoclave was removed from the oil bath, and cooled in a cold-water bath. Then, an aliquot (0.4 ml) was taken, diluted with MTBE (5 ml), washed with aq. sat. NH₄Cl (5 ml), and filtered over a plug of celite and analyzed by GC.

TABLE 3

Hydrogenation of methyl benzoate using [RuCl₂(PP)(S,S-DPEN)]

| Test | PP | NN | Com/Base | GC yield |
|---|---|---|---|---|
| 1 | 2,2′-bis(diphenylphosphino)biphenyl (PPh₂/PPh₂) | (1S,2S)-1,2-diphenylethylenediamine (Ph/Ph with NH₂/NH₂) | 500/50000 | 60%[1] |

TABLE 3-continued

Hydrogenation of methyl benzoate using [RuCl₂(PP)(S,S-DPEN)]

| Test | PP | NN | Com/Base | GC yield |
|---|---|---|---|---|
| 2 | 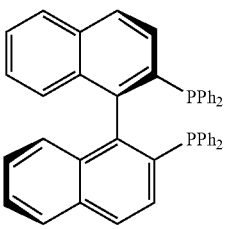 | 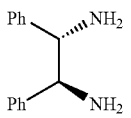 | 500/50000 | 73% |
| 3 | 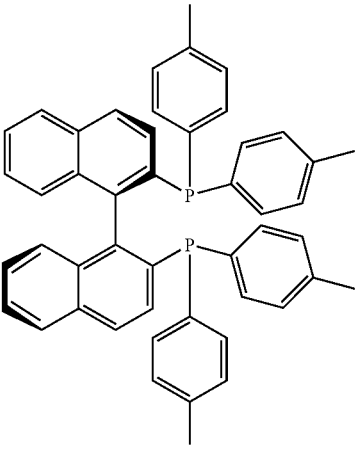 | 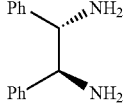 | 500/50000 | 78% |
| 4 | 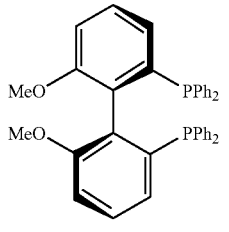 | 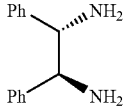 | 500/50000 | 69% |
| 5 | 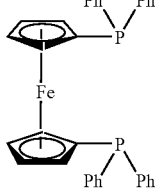 | 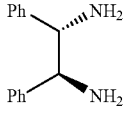 | 500/50000 | 47%[2] |
| 6 | 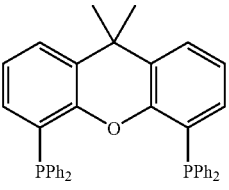 | 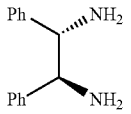 | 500/50000 | 39%[3] |

Com/Base: molar ratio in ppm relative to the substrate of complex and base.
GC yield versus internal standard (in %, analysed by GC) of benzyl alcohol. Reaction conditions: H₂ gas (50 bars), 60° C., 2 h, NaOMe as base and THF (2 M).
[1] Catalyst generated in-situ by pre-heating a solution of [Ru(TFA)₂(cod)] and the diphosphine in MTBE/THF (10/1) at 100° C. for 1 h and the solution used as is for the reaction.
[2] The preformed complex was used here.
[3] Catalyst generated in-situ by pre-heating a solution of [RuCl₂(pCym)]₂ with the diphosphine in EtOH/CH₂Cl₂ (4/1) at 50° C. for 30 minutes. Followed by solvent evaporation, and heating the residue with S,S-DPEN in THF at 140° C. for 1 h and the solution used as is for the reaction.

Example 4

Catalytic Hydrogenation of Esters Using Complex [RuCl$_2$(R-BINAP)(NN)]

General procedure for the catalytic hydrogenation of methyl benzoate as substrate:

Under argon, a Keim autoclave was charged with [RuCl$_2$(R-BINAP)(dmf)$_2$] (0.01 mmol, 0.05 mol %) and the diamine (0.01 mmol, 0.05 mol %) followed by THF (2 ml) and the solution stirred for 5 minutes. Then a solution of methyl benzoate (20 mmol) in THF (2 ml), followed by more THF (2×1 ml), and a solution of tridecane (1 mmol) in THF (2 ml), as internal standard, followed by more THF (2×1 ml), were successively added to the autoclave. Finally, solid NaOMe (1 mmol, 5 mol %) was added and the autoclave was pressurised with hydrogen gas at 50 bars and placed in a thermostatted oil bath set at the desired temperature. After the mentioned time, the autoclave was removed from the oil bath, and cooled in a cold-water bath. Then, an aliquot (0.4 ml) was taken, diluted with MTBE (5 ml), washed with aq. sat. NH$_4$Cl (5 ml), and filtered over a plug of celite and analyzed by GC.

TABLE 4

Hydrogenation of methyl benzoate using [RuCl$_2$(R-BINAP)(NN)]

| Test | NN | T [° C.]/time [h] | Com/Base | GC yield |
|---|---|---|---|---|
| 1 | PhCH$_2$NH-CH$_2$CH$_2$-NHCH$_2$Ph (out of the invention*) | 100/1 | 500/50000 | 0% |
| 2 | neopentyl-type diamine H$_2$NCH$_2$-C(CH$_3$)$_2$-CH$_2$NH$_2$ (out of the invention*) | 100/1 | 500/50000 | 0% |
| 3 | trans-1,2-diaminocyclohexane | 100/1 | 500/50000 | 19% |
| 4 | trans-1,2-diaminocyclohexane | 100/1 | 500/50000 | 31% |
|   |   | 60/2 | 500/50000 | 51% |
| 5 | Ph,Ph-diaminoethane (DPEN) | 100/1 | 500/50000 | 34% |
| 6 | Ph,Ph-diaminoethane (DPEN) | 100/1 | 500/50000 | 59% |
|   |   | 60/2 | 500/50000 | 73% |
| 7 | bis(4-F-phenyl)-diaminoethane | 60/2 | 500/50000 | 71% |
| 8 | bis(4-NMe$_2$-phenyl)-diaminoethane | 60/2 | 500/50000 | 60% |
| 9 | bis(1-naphthyl)-diaminoethane | 60/2 | 500/50000 | 71% |
| 10 | Ph,Ph-bis(N-methylamino)ethane (out of the invention*) | 60/2 | 500/50000 | 0% |

Com/Base: molar ratio in ppm relative to the substrate of complex and base.
GC yield versus internal standard (in %, analysed by GC) of benzyl alcohol. Reaction conditions: H$_2$ gas (50 bars), NaOMe as base and THF (2 M).
*included only as comparative matter

Example 5

Catalytic Hydrogenation of Various Esters Using Complex [RuCl$_2$(R-Binap)(S,S-DPEN)]

General procedure for the catalytic hydrogenation of methyl benzoate as substrate:

Under argon, a Keim autoclave was charged with [RuCl$_2$(R-BINAP)(dmf)$_2$] (0.01 mmol, 0.05 mol %) and S,S-DPEN (0.01 mmol, 0.05 mol %) followed by THF (2 ml) and the solution stirred for 5 minutes. Then a solution of the desired ester (20 mmol) in THF (2 ml), followed by more THF (2×1 ml), and a solution of tridecane (1 mmol) in THF (2 ml), as internal standard, followed by more THF (2×1 ml), were successively added to the autoclave. Finally, solid NaOMe (1 mmol, 5 mol %) was added and the autoclave was pressurised with hydrogen gas at 50 bars and placed in a thermostatted oil bath set at 60° C. After the mentioned time, the autoclave was removed from the oil bath, and cooled in a cold-water bath. Then, an aliquot (0.4 ml) was taken, diluted with MTBE (5 ml), washed with aq. sat. NH$_4$Cl (5 ml), and filtered over a plug of celite and analyzed by GC.

TABLE 5

Hydrogenation of various esters using complex [RuCl$_2$(R-BINAP)(S,S-DPEN)]

| Test | Ester | time [h] | Com/Base | GC |
|---|---|---|---|---|
| 1 | 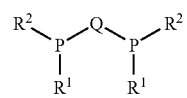 | 2 | 500/50000 | 77% (73%) |
| 2 | | 2 | 500/50000 | 61% (66%) |
| 3 | 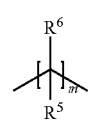 | 16 | 500/50000 | 51% |
| 4 |  | 16 | 500/50000 | 93% |

Com/Base: molar ratio in ppm relative to the substrate of complex and base.
GC: percent of product analysed by GC in the crude reaction mixture. Reaction conditions: H$_2$ gas (50 bars), 60° C., NaOMe as base and THF (2 M).

The invention claimed is:

1. A process for the reduction by hydrogenation, using molecular H$_2$, of a C$_3$-C$_{70}$ substrate containing one, two or three esters, or lactones, functional groups into the corresponding alcohol, or diol, characterized in that said process is carried out in the presence of a base and at least one catalyst or pre-catalyst of the general formula $$[Ru(PP)(NN)(S)_{2-n}Y_n](Y)_{2-n} \quad (1)$$

wherein n represents 0, 1 or 2;
S represents a neutral C$_1$-C$_{26}$ neutral monodentate ligand;
PP represents a C$_6$-C$_{60}$ bidentate ligand wherein the coordinating groups are two phosphino groups;
NN represents a C$_3$-C$_{40}$ bidentate ligand wherein the coordinating groups are two amino groups, at least one of said amino groups is a primary amine, and wherein at least one of the carbon atoms to which one of said amino group is bound (the α-carbon) is not a CH$_3$— or —CH$_2$— group; and each Y represents, simultaneously or independently, a hydrogen or halogen atom, a BH$_4$ or AlH$_4$ group, a hydroxyl group, or a C$_1$-C$_6$ alkoxy or carboxylic radical.

2. The process according to claim 1, wherein the catalyst or pre-catalyst is of the general formula $$[Ru(PP)(NN)Y_2] \quad (2)$$

wherein PP, NN and Y are as defined in claim 1.

3. The process according to claim 1, wherein the bidentate PP ligand is an optically active compound of formula

(3)

wherein
R$^1$ and R$^2$, when taken separately, represent, simultaneously or independently, a linear, branched or cyclic C$_1$ to C$_8$ alkyl or alkenyl group optionally substituted, a C$_6$ to C$_{10}$ aromatic group optionally substituted, or an OR$^3$ or NR$^3$R$^4$ group, R$^3$ and R$^4$ being a C$_1$ to C$_8$ alkyl or alkenyl group; the groups R$^1$ and R$^2$, bonded to the same P atom, when taken together, may form a saturated or unsaturated ring optionally substituted, having 5 to 10 atoms and including the phosphorus atom to which said R$^2$ and R$^1$ groups are bonded; and Q represents:
a group of formula

(i)

wherein m is an integer from 1 to 5, and
R$^5$ and R$^6$ represent, simultaneously or independently, a hydrogen atom, a linear, branched or cyclic C$_1$ to C$_{10}$ alkyl or alkenyl group optionally substituted, a C$_6$-C$_{10}$ aromatic group optionally substituted, or an OR$^7$ or NR$^7$R$^8$ group, R$^7$ and R$^8$ being a linear, branched or cyclic C$_1$ to C$_{10}$ alkyl or alkenyl group; two distinct R$^6$ and/or R$^5$ groups, taken together, may form a C$_5$ to C$_8$, or even up to C$_{10}$, saturated ring optionally substituted, including the carbon atoms to which each of said R$^6$ or R$^5$ group is bonded; or
a group of formula (ii)

wherein m is an integer from 2 to 4, and
two distinct adjacent R$^9$ groups, taken together, form a C$_5$ to C$_8$, or even up to C$_{10}$, aromatic ring optionally substituted or a C$_5$-C$_{12}$ metallocenediyl optionally substituted, including the carbon atoms to which each of said R$^9$ group are bonded; or
three distinct adjacent R$^9$ groups, taken together, form a naphthalene ring optionally substituted, including the carbon atoms to which each of said R$^9$ groups are bonded.

4. The process according to claim 3, wherein the bidentate PP ligand is of formula (3) wherein R$^1$ and R$^2$ represent, simultaneously or independently, a linear, branched or cyclic C$_1$ to C$_6$ alkyl group optionally substituted, a phenyl or naphthyl group optionally substituted; the groups R$^1$ and R$^2$, bonded to the same P atom, taken together, form a saturated or unsaturated ring optionally substituted, having 5, 6 or 7 atoms and including the phosphorus atom to which said R$^1$ and R$^2$ groups are bonded; and Q represents:

a group of formula

(iv)

wherein m is an integer from 1 to 3, and two distinct adjacent R$^9$ groups, taken together, form a C$_5$ to C$_{10}$ aromatic ring optionally substituted or a C$_5$-C$_{12}$ ferrocenediyl optionally substituted, including the carbon atoms to which each of said R$^9$ group are bonded; or three distinct adjacent R$^9$ groups, taken together, form a naphthalene ring optionally substituted, including the carbon atoms to which each of said R$^9$ group are bonded.

5. The process according to claim 3, wherein the ligand of formula (3) comprises one of the moieties:

a metallocene-1,1'-diphosphine of formula

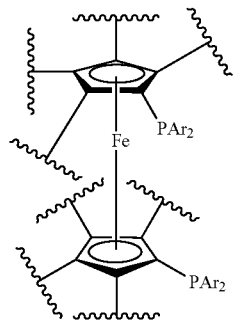

(A)

a α, α'-bis(naphthalene)-β,β'-diphosphine of formula

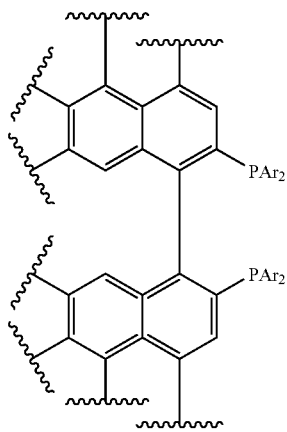

(B)

or a α,α'-bis(benzene)-β,β'-diphosphine of formula

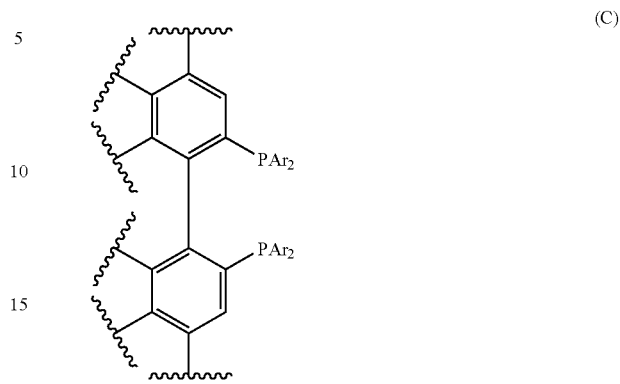

(C)

wherein each Ar represents a C$_6$ to C$_{10}$ aromatic group optionally substituted by one or two halogens, CF$_3$ groups or C$_1$ to C$_5$ alkoxy or polyalkyleneglycols groups, COOR$^d$, NR$^d_2$ or R$^d$ groups, wherein R$^d$ is a C$_1$ to C$_4$ alkyl, or a C$_{5-6}$ cycloalkyl, aralkyl or aromatic group.

6. The process according to claim 1, wherein the ligand NN is of formula

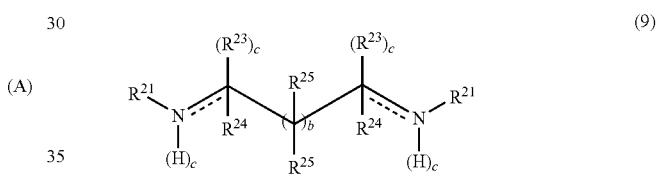

(9)

wherein the dotted line indicates a single or double bond, provided that only one dotted line per nitrogen atom may indicate a double bond;

b represents 0, 1 or 2;

R$^{21}$ represents a hydrogen atom or a R$^{21'}$R$^{22}$CH group, or, if the dotted line indicates a single bond may also represent a R$^{21'}$R$^{22}$C= group;

c is 0 or 1 when the carbon-nitrogen bond with the dotted line represents a single or double bond respectively; and R$^{21'}$, R$^{22}$, R$^{23}$, R$^{24}$, and R$^{25}$ represent, simultaneously or independently, a hydrogen atom, a linear, branched or cyclic C$_1$ to C$_{10}$ alkyl or alkenyl group optionally substituted, a C$_6$-C$_{10}$ aromatic group optionally substituted; R$^{21'}$ and R$^{24}$, taken together, may form a saturated or unsaturated heterocycle, optionally substituted and optionally containing one or two additional nitrogen or oxygen atoms, containing 5 to 10 atoms and including the carbon atoms and the N atom to which said R$^{21'}$ or R$^{24}$ are bonded; R$^{23}$ and R$^{24}$, or R$^{24}$ and R$^{25}$, when taken together, form a saturated or unsaturated ring optionally substituted, having 5 to 12 atoms and including the carbon atom to which said R$^{23}$, R$^{24}$ or R$^{25}$ groups are bonded; with the proviso that at least one of said R$^{23}$ or R$^{24}$ groups are not a hydrogen atom;

provided that at least one R$^{24}$ or R$^{22}$ is not a hydrogen atom, and provided that at least one coordinating amino group is a primary amine.

7. The process according to claim 6, wherein the ligand NN is of formula

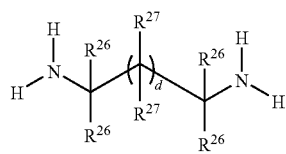

(12)

wherein d represents 0 or 1; and
$R^{26}$ or $R^{27}$ represents each a hydrogen atom or a linear, branched or cyclic $C_1$ to $C_6$ alkyl group or a phenyl group optionally substituted; two $R^{26}$, or one $R^{26}$ and one adjacent $R^{27}$, taken together, may form a $C_3$-$C_5$ alkanediyl or alkenediyl;
provided that at least one $R^{26}$ or is not a hydrogen atom.

8. The process according to claim 6, wherein the NN ligand is a compound of one of the formulae

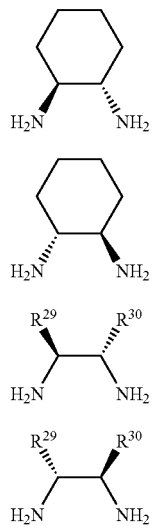

(12′)
(12″)
(12‴)
(12⁗)

wherein $R^{29}$ represents a $C_1$-$C_6$ alkyl group or a phenyl group optionally substituted, as defined above for $R^{28}$, and $R^{30}$ represents a hydrogen atom or a $R^{29}$ group.

9. The process according to claim 1, wherein any one or both of the ligands PP or NN is in an optically active form.

10. The process according to claim 1, wherein the base is selected in the group consisting of an alkaline or alkaline-earth metal carbonate, an alkaline or alkaline-earth metal hydroxide, a $C_{1-10}$ amidure, a $C_{10-26}$ phosphazene, and an alcoholate of formula $(R^{31}O)_2M$ or $R^{31}OM'$, wherein M is an alkaline-earth metal, M' is an alkaline metal or an ammonium $NR^{32}_4{}^+$, $R^{31}$ stands for hydrogen or a $C_1$ to $C_6$ linear or branched alkyl radical and $R^{32}$ stands for a $C_1$ to $C_{10}$ linear or branched alkyl radical.

11. The process according to claim 1, wherein the catalyst or pre-catalyst is specifically [RuCl$_2$(PP)(S,S-(1,2-diphenyl-1,2-ethyenediamine)] wherein:
S represents a neutral $C_1$-$C_{26}$ neutral monodentate ligand; and
PP is a α,α'-bis(naphthalene)-β,β'-diphosphine of formula:

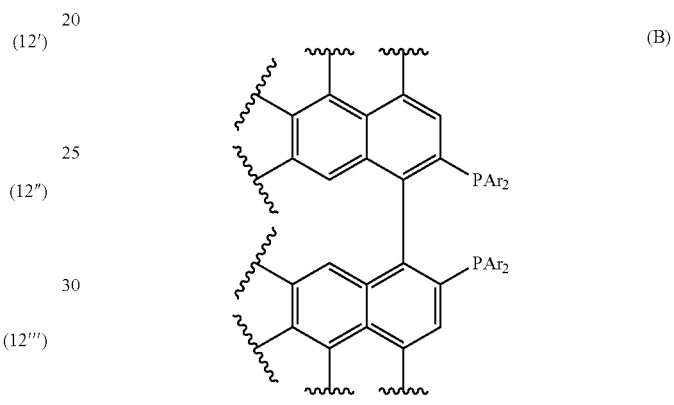

(B)

wherein each Ar represents a $C_6$ to $C_{10}$ aromatic group optionally substituted by one or two halogens, CF$_3$ groups or $C_1$ to $C_5$ alkoxy or polyalkyleneglycols groups, COOR$^d$, NR$^d_2$ or R$^d$ groups, wherein R$^d$ is a $C_1$ to $C_4$ alkyl, or a $C_{5-6}$ cycloalkyl, aralkyl or aromatic group.

12. The process according to claim 11, wherein, in the catalyst or pre-catalyst, each of the Ar substituents of PP represents a phenyl group.

* * * * *